(12) United States Patent
Steimle et al.

(10) Patent No.: US 10,302,565 B2
(45) Date of Patent: May 28, 2019

(54) SYSTEM AND METHOD FOR ISOTOPIC ANALYSIS OF CALCIUM USING LASER INDUCED FLUORESCENCE

(71) Applicant: ARIZONA BOARD OF REGENTS ON BEHALF OF ARIZONA STATE UNIVERSITY, Scottsdale, AZ (US)

(72) Inventors: Timothy Steimle, Tempe, AZ (US); Ariel Anbar, Scottsdale, AZ (US); Joseph Skulan, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/118,981

(22) PCT Filed: Feb. 18, 2015

(86) PCT No.: PCT/US2015/016275
§ 371 (c)(1),
(2) Date: Aug. 15, 2016

(87) PCT Pub. No.: WO2015/126881
PCT Pub. Date: Aug. 27, 2015

(65) Prior Publication Data
US 2017/0052116 A1    Feb. 23, 2017

Related U.S. Application Data

(60) Provisional application No. 61/941,913, filed on Feb. 19, 2014.

(51) Int. Cl.
*G01N 21/64* (2006.01)

(52) U.S. Cl.
CPC ....... *G01N 21/6402* (2013.01); *G01N 21/645* (2013.01); *G01N 21/6486* (2013.01);
(Continued)

(58) Field of Classification Search
CPC ............ G01N 21/6402; G01N 21/645; G01N 21/6486; G01N 2201/06113; G01N 2201/067
See application file for complete search history.

(56) References Cited

U.S. PATENT DOCUMENTS 3,826,364 A * 7/1974 Bonner ................. B07C 5/3425
209/3.1
4,573,796 A * 3/1986 Martin ............... G01N 15/1429
250/461.2
(Continued)

FOREIGN PATENT DOCUMENTS

JP    2002-071557    3/2002
KR    10-2006-0093785    8/2006

OTHER PUBLICATIONS

The International Search Report and Written Opinion dated Jun. 18, 2015 for International Application No. PCT/US2015/016275.

*Primary Examiner* — Marcus H Taningco
(74) *Attorney, Agent, or Firm* — Yakov S. Sidorin; Quarles & Brady LLP

(57) ABSTRACT

Laser-induced fluorescence based optical system and method configured to precisely quantify the relative abundances of calcium (Ca) isotopes in a sample. Optionally, a diode laser is used as a laser source, with its output frequency shifted by two electro-optical modulators to optically excite fluorescence in the calcium-containing sample. The amounts of fluorescence emitted by the various isotopes are measured and compared.

18 Claims, 2 Drawing Sheets

(52) U.S. Cl.
CPC .................. *G01N 2201/067* (2013.01); *G01N 2201/06113* (2013.01)

(56) References Cited

U.S. PATENT DOCUMENTS

| | | | |
|---|---|---|---|
| 5,504,337 A * | 4/1996 | Lakowicz | G01N 15/1434 250/459.1 |
| 5,760,900 A * | 6/1998 | Ito | G01N 15/1434 250/461.2 |
| 9,116,353 B2 * | 8/2015 | Sangu | G02B 21/16 |
| 2004/0239923 A1 * | 12/2004 | Adams | G01J 3/28 356/317 |
| 2008/0116389 A1 | 5/2008 | Hacker et al. | |
| 2009/0250615 A1 * | 10/2009 | Oldham | G01N 21/6428 250/362 |
| 2010/0067103 A1 * | 3/2010 | Sangu | G02B 21/16 359/385 |
| 2011/0309887 A1 | 12/2011 | Maki et al. | |
| 2013/0301664 A1 | 11/2013 | Prather et al. | |

* cited by examiner

SYSTEM AND METHOD FOR ISOTOPIC ANALYSIS OF CALCIUM USING LASER INDUCED FLUORESCENCE

CROSS-REFERENCE TO RELATED APPLICATIONS

The present application represents the U.S. National Stage of International Application No. PCT/US2015/016275, filed Feb. 18, 2015 which claims priority from and benefit of U.S. Provisional Patent Application Ser. No. 61/941,913, filed Feb. 19, 2014 and titled "System and Method for Isotopic Analysis of Calcium Using Laser-Induced Fluorescence". The disclosure of each the above-identified patent applications is incorporated herein by reference in its entirety.

TECHNICAL FIELD

The present invention is directed at detecting the relative abundance of certain chemical isotopes (for example, isotopes of calcium) with the use of laser-induced fluorescence and, in particular, at the laser-induced fluorescence based isotopic analysis of materials with the use of solid state laser sources and electro-optical modulators.

BACKGROUND

The relative concentrations of various calcium isotopes can be an important diagnostic marker for a variety of medical conditions. For example, the ratio of 44 Ca to 40 Ca in human blood or urine can provide important diagnostic information regarding bone mineral balance, making it possible to track and/or diagnose certain metabolic bone diseases and track the impact of treatments. As a difference example, monitoring bone mineral balance is useful for detecting bone density loss, which may have applications for maintaining health during long space missions. The ability to assess quickly and accurately relative abundance of calcium isotopes in chosen samples also has applications beyond the medical diagnostic fields, for example, in geochemistry, planetary science, climate science, and other fields.

Currently, calcium isotopic analysis is performed using mass-spectrometry, and, specifically, thermal-ionization mass-spectrometry or multiple collector inductively coupled mass-spectrometry. While effective, such techniques provide a typically slow analysis and employ costly equipment that requires sophisticated supporting infrastructure and technical expertise. As a result, conventional methods are generally unsuited for use outside of a laboratory environment.

SUMMARY

Embodiments of the invention are directed to using a judiciously structured laser-induced fluorescence system and method to detect the relative abundance of isotopes present in a sample, for example, the relative abundance of 40 Ca and 48 Ca in a calcium-containing sample. In particular, embodiments of the invention use a diode laser and one or more electro-optical modulators to optically probe a calcium-containing sample at wavelengths for which intrinsic fluorescence may be expected for certain isotopes. The idea of the invention stems from the realization that the measurement of the relative abundance of the isotopes is operationally insensitive to the fluctuations in light output of the laser source in the system of the invention.

In one embodiment, the invention uses a diode laser emitting at or about 657 nm. The output of the diode laser is split into two input signals, which are provided to a first and a second electro-optical modulator ("EOM"), respectively. The first electro-optical modulator phase modulates the supplied signal resulting in a first probe signal having a first wavelength corresponding to a fluorescence wavelength characteristic of a first isotope of interest. Similarly, the second electro-optical modulator phase modulates the input signal resulting in a second probe signal having a second wavelength corresponding to a fluorescence wavelength characteristic of a second isotope of interest. The modulated signals are supplied to a sample carrying a substance to be measured for the presence of the isotopes of interest. The fluorescence signals emitted by the isotopes of interest are then detected by a first and second optical detector (e.g., photodiodes, photomultiplier tubes, etc.), which generate electrical signals proportional to the detected optical fluorescence. These signals may be compared to determine the relative abundance of the isotopes of interest.

In another embodiment, directed to measuring the relative abundance of 40 Ca and 48 Ca, the laser diode and the first EOM are configured to a supply a first probe signal having a wavelength corresponding to a fluorescence wavelength characteristic of 40 Ca and the laser diode and the second EOM are configured to a supply a second probe signal having a wavelength corresponding to a fluorescence wavelength characteristic of 48 Ca. In certain embodiments, the nominal wavelength of the diode laser is selected to correspond to a fluorescence wavelength characteristic of 44 Ca. In these embodiments, the fluorescence signal emitted by the excited 44 Ca is used to monitor the frequency stability of the laser and provide feedback to dynamically tune the laser and lock it to its nominal emission wavelength.

In one embodiment, the invention is directed to a system for detecting the relative abundance of isotopes in a sample column, each isotope having a characteristic fluorescence wavelength. The system includes a laser having an output wavelength, a first electro-optical modulator arranged to receive a light beam from the laser, and to output a frequency shifted first probe beam having a first wavelength. The system further includes a second electro-optical modulator arranged to receive a light beam from the laser, and to output a frequency shifted second probe beam having a second wavelength. The system further includes a sample column including a substance having a plurality of isotopes to be measured, a first detector arranged to measure fluorescence induced in a first isotope by the first probe beam, and a second detector arranged to measure fluorescence induced in a second isotope by the second probe beam.

In another embodiment, the laser is a diode laser. In yet another embodiment, the system includes a beamsplitter optically arranged between an output of the laser and the first electro-optical modulator. In another embodiment the system has a mirror optically arranged between an output of the laser and the second electro-optical modulator. In other embodiments, the first and second probe beams are arranged to intersect the sample column at right angles. In some embodiments, the first detector has a field of view that does not include a region of intersection between the first probe beam and the sample column, and in some embodiments, the second detector has a field of view that does not include a region of intersection between the second probe beam and the sample beam. In another embodiment, the laser is arranged to provide a non-frequency shifted beam to the sample column such that fluorescence is excited at the output wavelength, and further including a third detector arranged to detect fluorescence excited at the laser's output wavelength.

Another embodiment is directed to a method of determining the relative abundance of isotopes in a sample. The method involves providing a laser having an output beam having an output wavelength, splitting the output beam into at least a first and second beams, and frequency shifting the first beam with a first electro-optical modulator resulting in a first probe beam. The method further includes frequency shifting the second beam with a second electro-optical modulator resulting in a second probe beam, exciting fluorescence in the sample with the first probe beam and measuring a resulting quantity of first fluorescence light, exciting fluorescence in the sample with the second probe beam and measuring a resulting quantity of second fluorescence light and comparing the quantity of first fluorescence light and second fluorescence light.

In certain embodiments, the wavelength of the first probe beam is chosen to excite fluorescence in a first isotope and the wavelength of the second probe beam is chosen to excite fluorescence in a second isotope. In some embodiments, the first isotope is 40 Ca and the second isotope is 48 Ca. In certain embodiments, exciting fluorescence in the sample with the first probe beam comprises intersecting the first probe beam with a sample column including the sample. In some embodiments, measuring a resulting quantity of first fluorescence light excludes intercepting light directly from a point of intersection of the first probe beam with a sample column. In some embodiments, measuring a resulting quantity of second fluorescence light excludes intercepting light directly from a point of intersection of the second probe beam with a sample column.

In some embodiments, the method includes exciting fluorescence in the sample with light from the laser at the output wavelength. In other embodiments, the output wavelength is chosen to excite fluorescence in a third isotope of the sample. Other embodiments include measuring a resulting quantity of third fluorescence light resulting from excitation of the third isotope, and some embodiments include using a time-varying quantity of third fluorescence light to adjust the output wavelength of the laser.

Embodiments of the invention have certain advantages over conventional methods for measuring the relative abundance of calcium isotopes. In contrast to the conventional mass spectrometry, for example, the methods and systems of the instant invention can be realized with more robust, low-cost, compact and low-mass components. This facilitates field deployment of the proposed system(s), and, possibly even space deployment for space-based bone density monitoring. Systems according to embodiments of the invention also have advantages over alternative systems used measurement of relative abundance of calcium isotopes in a sample. For example—and in contradistinction with the use of a system employing a broadband tunable laser source (which facilitates selective excitation of fluorescence in a calcium sample)—the use of single laser source that selectively probes the sample through EOMs makes the embodiments of the present system insensitive to laser-power fluctuations. Additionally, by using a central nominal wavelength, that is frequency-shifted by two EOMs, the excited fluorescence can be used to provide frequency feedback for the laser source.

Embodiments of the invention also have higher detection sensitivity than conventional mass-spectrometric methods. In mass-spectrometry, the detected ion is captured during the detection process as a result of which each detected ion causes only one detectable event. In contrast, during the process of laser-induced fluorescence the excited atom returns to its initial quantum level from which it can be excited again (i.e., at the Rabi frequency). Consequently, one atom measured according to the proposed methodology of laser-induced fluorescence can generate multiple (for example—thousands of) signals (i.e., photons), thereby increasing the system response to a triggering occurrence.

BRIEF DESCRIPTION OF THE DRAWINGS

The features of the present invention are further illustrated with the following generally not-to-scale drawings, of which.

DETAILED DESCRIPTION

Embodiments of the invention re described in reference to the generally-not-to-scale Figures, in which like numbers represent the same or similar elements and units. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. The invention as recited in claims appended to this disclosure is intended to be assessed in light of the disclosure as a whole, including features disclosed in prior art to which reference is made.

The term "LIFIA system" used herein and in appended claims refers to and defines an optical system configured/structured to detect the relative abundance of isotopes in a sample by implementing a principle of laser-induced fluorescence.

Figure 1:
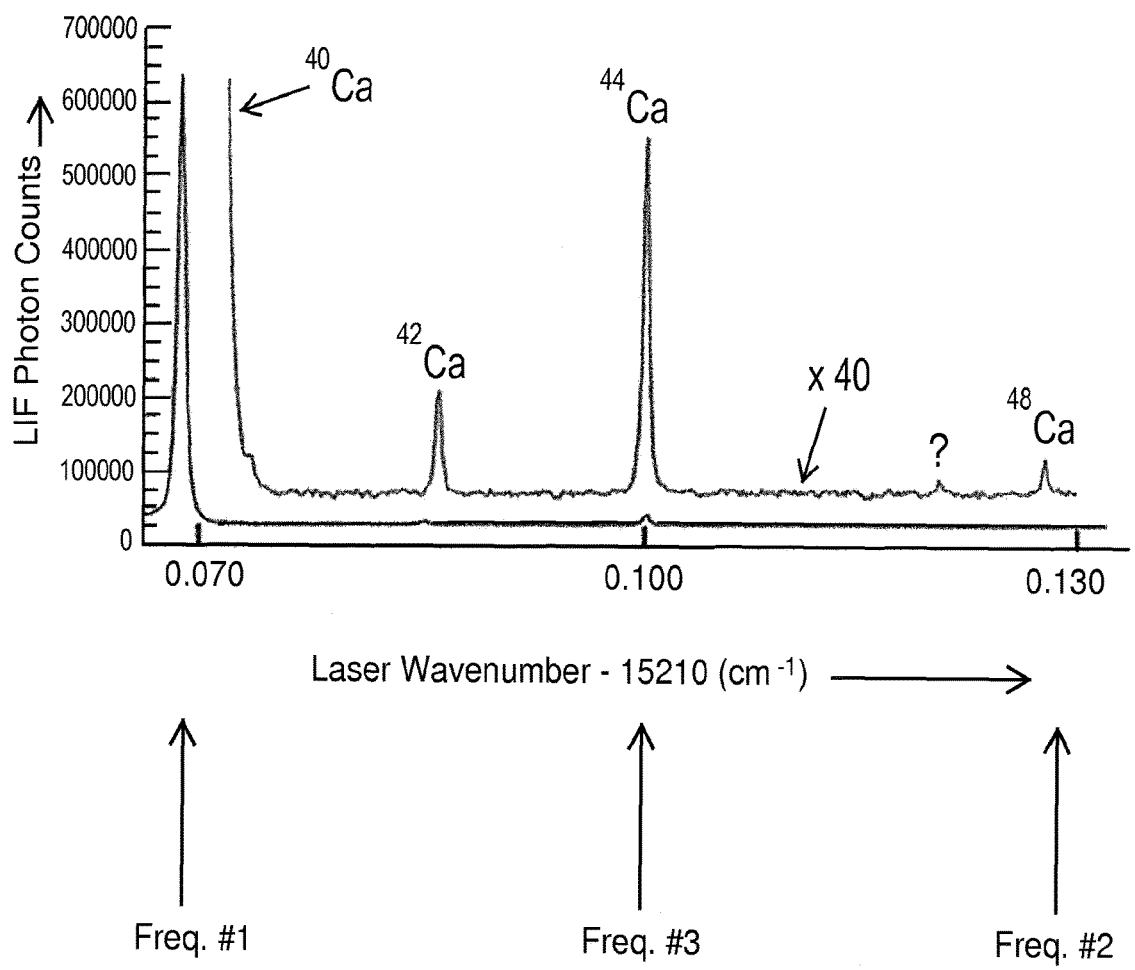
FIG. 1 is a plot of the laser-induced fluorescence spectrum for the 657 nm transitions of calcium.

FIG. 1 provides a plot showing the laser induced fluorescence spectrum for the 657 nm transitions of calcium. The data are presented as laser induced photon counts recorded by a an optical detector system (in this case, including a photo-multiplying tube or PMT) as a function of excitation/fluorescence emission wavelength in units of wavenumber (cycles per cm). The spectrum of FIG. 1, empirically acquired by employing a tunable dye laser as an excitation source, demonstrates that individual fluorescence emission peaks associated with various isotopes of interest can be isolated and identified (such as, for example, the 40 Ca transition at 15210.069 cm-1, the 44 Ca transition at 15210 cm-1, and the 48 Ca transition at 15210.120 cm-1). The data representing relative abundance values for various isotopes are determined from the ratio of the integrated area under one emission peak with that under another emission peak.

Figure 2:
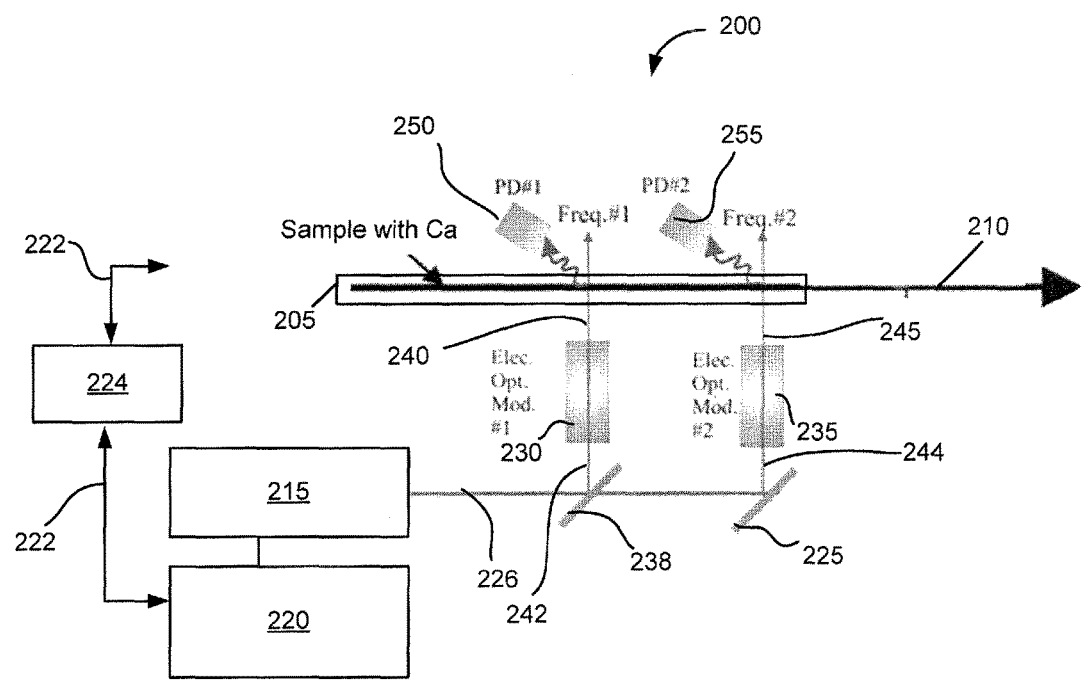
FIG. 2 is a schematic diagram of a system for determining the relative abundance of two isotopes of interest in a sample of calcium according to an embodiment of the invention.

FIG. 2 schematically illustrates an arrangement for measuring the relative abundance of calcium isotopes using a LIFIA system 200. As shown, a sample 210 (such as a sample beam or column) including vaporized calcium under low-pressure is being characterized/measured. Optionally, the sample 210 (such as a sample column) is confined in a tubular sample chamber 205. The sample may originate from a sample of, for example, urine or blood (in which case the calcium isotopes will be characterizing such sample of urine or blood). A fixed frequency (or, in a different implementation, frequency-tunable such as, for example, temperature tunable) laser 215 (in one embodiment—a diode laser) is used as a source of input light, driven by a laser power supply 220. Both the operation of the laser source and the acquisition of empirical data procured with the system 200 are governed (as schematically shown by arrows 222) by programmable electronic circuitry unit 224, which may include both a computer-readable processor and tangible, non-transitory computer-readable storage medium used for storing at least one of computer code(s) configured to drive the system 200 to acquire optical data, as discussed below, and to process such acquired data to extract sought after information about.

The laser 215 is judiciously chosen to generate output light 226 with spectrum defined such as to cause excitation of fluorescence in the calcium sample. The spectrum includes an operational wavelength of the laser 215. Excitation of fluorescence in the sample 210, in one example, occurs in the sample in the vicinity of the 657 nm transitions (or in the vicinity of the 423 nm transitions, in another example) by illuminating the sample 210 either directly with the output light or with light formed from the output light with a non-linear frequency conversion method. The light output 226 produced by the laser source 215 is directed to and is received, as an input, by at least one of the first electro-optical modulator (EOM) 230 and the second EOM 235. The optical train of components between the laser 215 and the EOMs, 230, 235 includes a beamsplitter 238 (which, in one example, may be optimized for a 50% reflection and a 50% transmission at the angle of installation and the laser wavelength) and a reflector 225. The reflective characteristics of the beamsplitter 238 and reflector 225 are selected such that the powers of the first and second probe beams 240, 245 (formed by portions 242, 244 of the laser output 226 upon passing through the EOMs 230, 235 and discussed more fully below) are equal when these beams reach the sample 210.

The first EOM 230 is configured to phase-modulate the input beam 242 to form a sideband frequency-shifted first probe signal beam 240 and direct this beam towards the sample 215. The operational characteristics of the EOM 230 are judiciously chosen to ensure that, for a given set of optical parameters of the light portion 242, the wavelength of the first probe beam 240 is defined to excite fluorescence in a first isotope contained in the sample 210. In one embodiment, the first probe light beam 240 is defined to excite the 40 Ca transition, and so has a nominal wavelength of 657.45943929 nm. The second EOM 235 is configured to phase-modulate the input beam to form a sideband frequency-shifted second probe light beam 245 and to direct it towards the sample 210. The operational characteristics of the EOM 235 are judiciously chosen to ensure that, for a given set of optical parameters of the light portion 244, the wavelength of the second probe light beam 245 is defined to excite fluorescence in a second isotope contained in the sample 215. In one embodiment, second probe light beam 245 is defined to excite the 48 Ca transition, and so has a nominal wavelength of 657.45943652 nm. When the sample 210 includes a sample column, the system 200 is spatially configured such that the first and second probe light beams 240, 245 intersect the sample column 210 perpendicularly (transversely, in general) to the direction of flow of the sample column 210.

The system 200 further includes a first optical detector 250 arranged to detect fluorescence excited in the sample 210 by the first probe beam 240, and a second optical detector 255 arranged to detect fluorescence excited in the sample 210 by the second probe beam 245. The first and second optical detectors 250, 255 may be photodiodes, PMTs, or any other optical detectors having sensitivity, dynamic range and temporal response sufficient to detect laser-induced fluorescence in calcium.

To facilitate and improve the quality of the detection of laser-induced fluorescence, and the rejection of noise, the output 226 of the laser 215 may optionally be temporally modulated (for example, with the use of the circuitry 224). Additional spectral filters, optical elements, stops and straylight baffles (not shown) may also be used between the detectors 250, 255 and the sample 210 to reduce optical noise caused by unwanted scattering and/or reflections of light. Such reduction can be achieved by, for example, restricting the fields of view of detectors 250, 255 and/or by imaging a point of intersection of at least one of the probe beams 240, 245 and the sample 210 directly onto the corresponding detector.

Each of the detectors 250, 255 generates a corresponding electrical signal output proportional to the irradiance at the detector, which can be sampled in the circuitry 224 for the following data analysis. By comparing the electronic signal output generated by the detectors 250 and 255, the relative abundance of the sought after isotopes (such as, for example, isotopes 40 Ca and 48 Ca) is determined as the ratio of the integrated area under one isotope emission peak with that under another isotope emission peak.

Because the decay time for calcium's 657 nm transitions is relatively long, and depending on the speed of the sample column, the excited fluorescence signal may be detected "downstream" of the point of intersection between the probe signals 240, 245 and the sample 210. This may be accomplished by spatially orienting the detectors 250, 255 such that their respective fields of view cover a location "downstream" of the point of intersection of the probe beams and the sample column. Preventing or excluding light from the point of intersection of the probe beams and the sample column from reaching the detectors has the advantage of increasing signal to noise ratio as direct scattered light from the probe beam is excluded from the measurement.

Notably, the system 200 of FIG. 2 has additional advantages. Because the fluorescent light produced by both the 40 Ca and the 48 Ca are caused by the same laser output 226, the proposed measurement methodology is insensitive to changes and/or fluctuations in the laser output 226 (since any such change will appear on both measurement channels and will be dropped out of the measured ratio). Additionally, the timing of data capture between the first and the second detectors may be adjusted and/or offset such that the data streams from the two detectors are synchronized to the same position on the sample column. In other words, the data stream from the first detector may be delayed by the amount of time necessary for the sample column to advance from the first probe beam's point of intersection with the sample 210 to the second probe beam's point of intersection with the sample 210. Such synchronization ensures that the second detector 255 is measuring the fluorescence generated at same location on the sample column as that measured by the first detector 250. This makes the arrangement insensitive to variations in Ca concentration throughout the column.

In certain optional embodiments, a third detector (not illustrated in FIG. 2, above) may be used to provide feedback to frequency-lock the operation of the laser 215. In these embodiments, the nominal output wavelength of the laser 215 is selected to excite fluorescence characteristic of the 44 Ca 657 nm transition when the laser output 226 is directly delivered to the sample 210. A 44 Ca probe beam is then formed by spatially separating a portion of the beam 226 and directing it directly to the sample 210 to excite the 44 Ca fluorescence that is further monitored by such third detector. When the amplitude of this 44 Ca fluorescence signal begins to fall off, it is an indication that the nominal output of the laser 215 has begun to drift. In response, the laser's output wavelength is adjusted with the unit 224 until the amplitude of the 44 Ca fluorescence signal returns to the pre-determined value. Because the frequency shift provided by the EOMs is so stable, locking the laser output wavelength in this manner ensures that the correct wavelengths for the first and second probe beams 240, 245 are maintained.

It is appreciated, therefore, that a system of the invention is configured to detect the relative abundance of isotopes in a sample, each isotope having a characteristic fluorescence wavelength. Such system includes i) a first electro-optical modulator (EOM), of the system, configured to receive a first input beam of light and produce therefrom a first frequency-shifted probe beam of light having a first wavelength; ii) a second EOM, of the system, configured to receive a second input beam of light and produce therefrom a second frequency-shifted probe beam of light having a second wavelength; iii) a first detector positioned in optical communication with the first EOM to acquire first fluorescence induced in a first isotope of the sample when said sample is illuminated with the first probe beam, and iv) a second detector positioned in optical communication with the second EOM to acquire second fluorescence induced in a second isotope of the sample column when said column is illuminated with the second probe beam. The system may additionally include a laser configured to generate an output beam of light, such output beam of light including light present in at least one of the first and second input beams of light. The system may additionally include an optical reflector disposed between the laser and the first EOM and an optical reflector between the laser and the second EOM. When the sample is disposed in optical communication with the system, optical components of said system are spatially oriented and dimensioned such as to direct the first and second frequency-shifted probe beams to intersect the sample at right angles. In a specific case, when the sample is disposed in optical communication with the system, the first detector is structured to have a first field-of-view (FOV) that does not cover a region where the first frequency-shifted probe beam intersects the sample. Alternatively or in addition, in such a case the second detector may be structured to have a second FOV that does not cover a region of intersection where the second frequency-shifted probe beam intersects the sample. A laser source of the system may be chosen to generate a laser-output beam of light having such an output wavelength that, when such laser output beam is delivered to a sample that is disposed in optical communication with at least one of the first and second EOMs, the fluorescence is excited at the sample and the system may further contain a third optical detector positioned to detect this fluorescence.

It is also understood that the proposed method for determining the relative abundance of isotopes in a sample includes: (i) with a first electro-optical modulator (EOM), frequency-shifting a first portion of an input light beam having an input light beam wavelength to form a first probe beam having a first wavelength; (ii) with a second EOM, frequency-shifting a second portion of the input light beam having an input light beam wavelength to form a second probe beam having a second wavelength; (iii) acquiring first and second fluorescent light, respectively excited in a sample with the first and second probe beams, with an optical detector system; and (iv) comparing first and second values respectively representing amounts of the first and second fluorescent light acquired with the optical detector system. The method may additionally include forming first and second portions of the input light beam by spatially splitting an output beam of a laser. Alternatively or in addition, the method may include configuring the first and second EOMs to define the first and second probe beams with such first and second wavelengths (based on respectively corresponding frequency shifts of the input light beam wavelength) that respectively cause excitation of first and second fluorescent light in first and second isotopes of the sample. The step of comparing the first and second values may be effectuated without intercepting light directly from a point of intersection of the first probe beam with the sample and/or without intercepting light directly from a point of intersection of the second probe beam with the sample. The method may include a step of using data representing time-dependent variations of said third value to adjust the output wavelength of the laser.

While the preferred embodiments of the present invention have been illustrated in detail, it should be apparent that modifications and adaptations to those embodiments may occur to one skilled in the art without departing from the scope of the present invention as set forth in the following claims.

The invention claimed is:

1. A system configured to detect the relative abundance of isotopes in a sample, each isotope having a characteristic fluorescence wavelength, the system comprising:
   a first electro-optical modulator (EOM) of said system configured to receive a first input beam of light and produce therefrom a first frequency-shifted probe beam of light having a first wavelength;
   a second EOM of said system configured to receive a second input beam of light and produce therefrom a second frequency-shifted probe beam of light having a second wavelength;
   a first detector positioned in optical communication with the first EOM to acquire first fluorescence induced in a first isotope of the sample when said sample is illuminated with the first probe beam, and
   a second detector positioned in optical communication with the second EOM to acquire second fluorescence induced in a second isotope of the sample column when said column is illuminated with the second probe beam.

2. The system of claim 1, further comprising a laser configured to generate an output beam of light, said output beam of light including light present in at least one of the first and second input beams of light.

3. The system of claim 2, further including an optical reflector disposed between the laser and the first EOM.

4. The system of claim 2, further including a mirror between the laser and the second EOM.

5. The system of claim 1, wherein, when the sample is disposed in optical communication with the system, optical components of said system are spatially oriented and dimensioned such as to direct the first and second frequency-shifted probe beams to intersect the sample at right angles.

6. The system of claim 1, wherein, when the sample is disposed in optical communication with the system, the first detector has a first field-of-view (FOV) that does not cover a region where the first frequency-shifted probe beam intersects the sample.

7. The system of claim 6, wherein the second detector has a second FOV that does not cover a region of intersection where the second frequency-shifted probe beam intersects the sample.

8. The system of claim 1, comprising a laser configured to generate a laser-output beam of light having an output wavelength, said system being structured to deliver said laser-output beam of light to a sample that is disposed in optical communication with at least one of the first and second EOMs, and further comprising a third optical detector positioned to detect fluorescence excited at the sample by said laser-output beam of light at the output wavelength.

9. A method for determining the relative abundance of isotopes in a sample, the method comprising:

with a first electro-optical modulator (EOM), frequency-shifting a first portion of an input light beam having an input light beam wavelength to form a first probe beam having a first wavelength;

with a second EOM, frequency-shifting a second portion of the input light beam having an input light beam wavelength to form a second probe beam having a second wavelength;

acquiring first and second fluorescent light, respectively excited in a sample with the first and second probe beams, with an optical detector system; and comparing first and second values respectively representing amounts of the first and second fluorescent light acquired with the optical detector system.

10. The method of claim 9, further comprising forming first and second portions of the input light beam by spatially splitting an output beam of a laser.

11. The method of claim 9, further comprising configuring the first and second EOMs to define the first and second probe beams with such first and second wavelengths, based on respectively corresponding frequency shifts of the input light beam wavelength, that respectively cause excitation of first and second fluorescent light in first and second isotopes of the sample.

12. The method of claim 11, further comprising providing the sample containing 40 Ca as the first isotope and 48 C as the second isotope.

13. The method of claim 9, further comprising at least one of i) exciting the first fluorescent light in the sample with the first probe beam, and ii) exciting the second fluorescent light in the sample with the second probe beam.

14. The method of claim 13, wherein said comparing includes measuring said first value without intercepting light directly from a point of intersection of the first probe beam with the sample.

15. The method of claim 13, wherein said comparing includes measuring said second value without intercepting light directly from a point of intersection of the second probe beam with the sample.

16. The method of claim 9, further comprising exciting third fluorescent light in the sample with said input light beam at the input light beam wavelength.

17. The method of claim 16, further comprising defining the input light beam wavelength based on a third isotope present in the sample such as to cause said third isotope emit the third fluorescent light.

18. The method of claim 17, further comprising measuring, with the optical detector system, a third value representing amount of the third fluorescent light resulting from excitation of the third isotope with the input light beam.

* * * * *